United States Patent
Barrett et al.

(10) Patent No.: US 11,389,576 B2
(45) Date of Patent: Jul. 19, 2022

(54) DETERMINATION OF PATIENT BLOOD VOLUME AT START OF A DIALYSIS TREATMENT

(71) Applicant: Fresenius Medical Care Holdings, Inc., Waltham, MA (US)

(72) Inventors: Louis Leegrande Barrett, West Point, UT (US); Perry N. Law, Kaysville, UT (US); Douglas L. Cox, Morgan, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 778 days.

(21) Appl. No.: 16/207,980

(22) Filed: Dec. 3, 2018

(65) Prior Publication Data
US 2020/0171229 A1 Jun. 4, 2020

(51) Int. Cl.
*A61M 1/16* (2006.01)
*A61M 1/36* (2006.01)

(52) U.S. Cl.
CPC ........ *A61M 1/1603* (2014.02); *A61M 1/1615* (2014.02); *A61M 1/1621* (2014.02); *A61M 1/3656* (2014.02); *A61M 2205/3334* (2013.01); *A61M 2205/3379* (2013.01)

(58) Field of Classification Search
USPC ....... 210/85, 90, 96.2, 97, 143, 252, 321.71, 210/418, 420, 646, 647; 604/4, 65, 66; 607/60; 709/217
See application file for complete search history.

(56) References Cited

U.S. PATENT DOCUMENTS

| 5,372,136 A | 12/1994 | Steuer et al. |
| 8,792,089 B2 | 7/2014 | Zhang et al. |
| 9,814,412 B2 | 11/2017 | Zhang et al. |
| 2008/0103427 A1 | 5/2008 | Toyoda et al. |

FOREIGN PATENT DOCUMENTS

| CA | 2 949 679 A1 | 11/2015 | |
| WO | WO-9817193 A1 * | 4/1998 | .......... A61M 1/3653 |
| WO | WO 2015/179523 A1 | 11/2015 | |

OTHER PUBLICATIONS

International Patent Application No. PCT/US2019/048980, Search Report (dated Nov. 20, 2019).

* cited by examiner

*Primary Examiner* — Hayden Brewster
(74) *Attorney, Agent, or Firm* — Leydig, Voit & Mayer, Ltd.

(57) ABSTRACT

Embodiments of the disclosure provide a method for determining beginning blood volume of a patient during dialysis (e.g., hemodialysis). Ultrafiltration rates are determined at different time stamps during dialysis by obtaining a blood flowrate measurement and hematocrit measurements at input port and output port of a dialyzer connected to the patient. The flowrate and hematocrit measurements are used to determine fluid removed from the patient during dialysis. The ultrafiltration rates and fluid removed from the patient are used to determine the beginning blood volume of the patient.

8 Claims, 4 Drawing Sheets

DETERMINATION OF PATIENT BLOOD VOLUME AT START OF A DIALYSIS TREATMENT

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney. Conventional methods of performing dialysis are based on estimates of the amount of fluid which can be removed from a patient based on the patient's weight at the time of arrival for regular treatments. Rough estimates for a "target" weight are determined by algorithms using factors such as height, weight and other physiological conditions before a physician orders the dialysis treatment.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a special filter termed a "dialyzer." The dialyzer is intended to remove unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. These membranes feature small holes which are large enough to pass liquid and liquid based impurities—but are not large enough to pass red blood cells. The fresh dialysate collects excess impurities passing through the straw-like tubes by diffusion, and also collects excess water through an ultrafiltration process due to a pressure drop across the membranes. During this process, the red cell volume is preserved inside the straw-like tubes and recirculated back into the body. The used dialysate exits the dialyzer with the excess fluids and toxins via an output tube, thus cleansing the blood and red cell volume flowing through the dialyzer. The dialyzed blood then flows out of the dialyzer via tubing and a needle (or catheter) back into the patient. Sometimes, a heparin drip or pump is provided along the extracorporeal blood flow loop in order to prevent red cell clotting during the hemodialysis process. Several liters of excess fluid can be removed during a typical multi-hour treatment session. In the U.S., a chronic patient will normally undergo hemodialysis treatment in a dialysis center three times per week, either on Monday-Wednesday-Friday schedule or a Tuesday-Thursday-Saturday schedule. These in-center treatments are typically completed over 3 to 4 hours with blood flow rates typically above 300 ml/minute. In other countries, the flow rates and time for treatment are lower and longer, respectively.

Hemodialysis has an acute impact on the fluid balance of the body due in part to the rapid change in circulating blood volume. When the dialysis fluid removal rate is more rapid than the plasma refilling rate of the stored plasma held by the internal tissue of the body, intravascular blood volume decreases. The resulting imbalance has been linked to complications similar to conventional blood loss such as hypotension, loss of consciousness, headaches, vomiting, dizziness and cramps experienced by the patient, both during and after dialysis treatments. Continuous quantitative measurement of parameters relating to the processing of the blood volume (in real-time) during hemodialysis can reduce the chance of dialysis-induced hypotension, and otherwise optimize dialysis therapy regimens by controlling fluid balance and aiding in achieving the target dry weight for the patient.

Although dialysis involves fluid removal from a patient, there is no convenient way of obtaining an initial blood volume of the patient before treatment. A patient can go to a hospital or an in-patient facility to measure blood volume using dilution indicators. For example, a chemical sample is injected into the patient's blood and then a sample of the blood is extracted to determine concentration of the chemical sample in the blood using special equipment. Since dialysis clinics usually do not have a setup for using dilution indicators, blood volume obtained in this manner may be unhelpful because blood volume is a moving target. That is, before getting to a dialysis clinic, a patient that measured his blood volume beforehand may have lost blood volume from exercising or may have gained blood volume from eating lunch. Thus, the blood volume measurement obtained before reaching the dialysis clinic can be drastically different from the patient's actual blood volume at start of dialysis.

SUMMARY

An embodiment of the disclosure provides a system for determining beginning blood volume of a patient undergoing dialysis treatment. The system comprises: a first portion of tubing, configured to connect a patient to an input of a dialyzer; a second portion of tubing, configured to connect the patient to an output of the dialyzer; a pump, configured to pump blood from the patient through the first portion of tubing into the dialyzer, and out of the dialyzer into the second portion of tubing; a first blood chamber, disposed along the first portion of tubing, and a second blood chamber, disposed along the second portion of tubing, wherein the first blood chamber and the second blood chamber are configured to facilitate hematocrit measurement; and a controller, configured to determine the beginning blood volume using hematocrit values associated with the input of the dialyzer, hematocrit values associated with the output of the dialyzer, and a flowrate of blood through the first portion of tubing.

An embodiment of the disclosure provides a method for determining beginning blood volume of a patient connected to a dialysis system. The method comprises: circulating, using a pump of the dialysis system, blood from the patient through a dialyzer; and determining, using the dialysis system, beginning blood volume of the patient. Determining the beginning blood volume includes: (a) determining a blood flowrate corresponding to an input side of the dialyzer; (b) determining a fluid removal rate at an initial time via the blood flowrate, hematocrit corresponding to the input side of the dialyzer at the initial time and hematocrit corresponding to the output side of the dialyzer at the initial time; (c) determining a fluid removal rate after a first measurement period via the blood flowrate, hematocrit corresponding to the input side of the dialyzer after the first measurement period and hematocrit corresponding to the output side of the dialyzer after the first measurement period; (d) determining volume of fluid removed for the first measurement period via the fluid removal rate at the initial time and the fluid removal rate after the first measurement period; (e) determining fractional blood volume change via hematocrit corresponding to the input side of the dialyzer at the initial time and hematocrit corresponding to the input side of the dialyzer after the first measurement period; and (f) determining the beginning blood volume via the fractional blood volume change and the volume of fluid removed for the first measurement period.

An embodiment of the disclosure provides a non-transitory computer readable medium for determining beginning blood volume of a patient connected to a dialysis system. The non-transitory computer readable medium includes instructions for causing a processor of the dialysis system to facilitate performing: blood circulation, using a pump of the dialysis system, blood from the patient through a dialyzer; and determining, using the dialysis system, beginning blood volume of the patient. Determining the beginning blood volume includes: (a) determining a blood flowrate corresponding to an input side of the dialyzer; (b) determining a fluid removal rate at an initial time via the blood flowrate, hematocrit corresponding to the input side of the dialyzer at the initial time and hematocrit corresponding to the output side of the dialyzer at the initial time; (c) determining a fluid removal rate after a first measurement period via the blood flowrate, hematocrit corresponding to the input side of the dialyzer after the first measurement period and hematocrit corresponding to the output side of the dialyzer after the first measurement period; (d) determining volume of fluid removed for the first measurement period via the fluid removal rate at the initial time and the fluid removal rate after the first measurement period; (e) determining fractional blood volume change via hematocrit corresponding to the input side of the dialyzer at the initial time and hematocrit corresponding to the input side of the dialyzer after the first measurement period; and (f) determining the beginning blood volume via the fractional blood volume change and the volume of fluid removed for the first measurement period.

DETAILED DESCRIPTION

Embodiments of the disclosure provide a non-invasive method for determining patient blood volume during dialysis. Knowing a patient's blood volume at the start of dialysis allows for better, more effective treatment of the patient compared to using estimated benchmarks based on weight and height of the patient. The patient's blood volume at the start of dialysis can be tracked through various treatments to determine how the blood volume fluctuates over time. Blood volume at start of dialysis can also inform how long the dialysis treatment should last.

Blood volume at start of a dialysis treatment is a parameter currently not available to physicians in dialysis clinics. Thus embodiments of the disclosure provide a method of benchmarking the condition of dialysis patients at the beginning of their dialysis sessions without resorting to invasive dye and/or isotope methods. Dyes and isotopes are not practical for use in a dialysis clinic. These systems are not readily available in the clinics and the patients have inadequate time in the clinic based on the time required for dialysis to perform these measurements. In addition, the cost of this type of measurement can be prohibitive and would not be available for every treatment. Yet, due to the success of a dialysis treatment a patient may feel good after it and eat or drink improperly before the next session. Therefore, the clinician and physician have no readily available benchmark of the patient's fluid condition at the beginning of a treatment to gauge what adjustments need to be made in the next session for best fluid management. The embodiments disclosed here provide for the important benchmark of the patient's starting fluid level volume. Before describing embodiments of the disclosure, FIG. 1 shows an example setup for a hemodialysis treatment.

Figure 1:
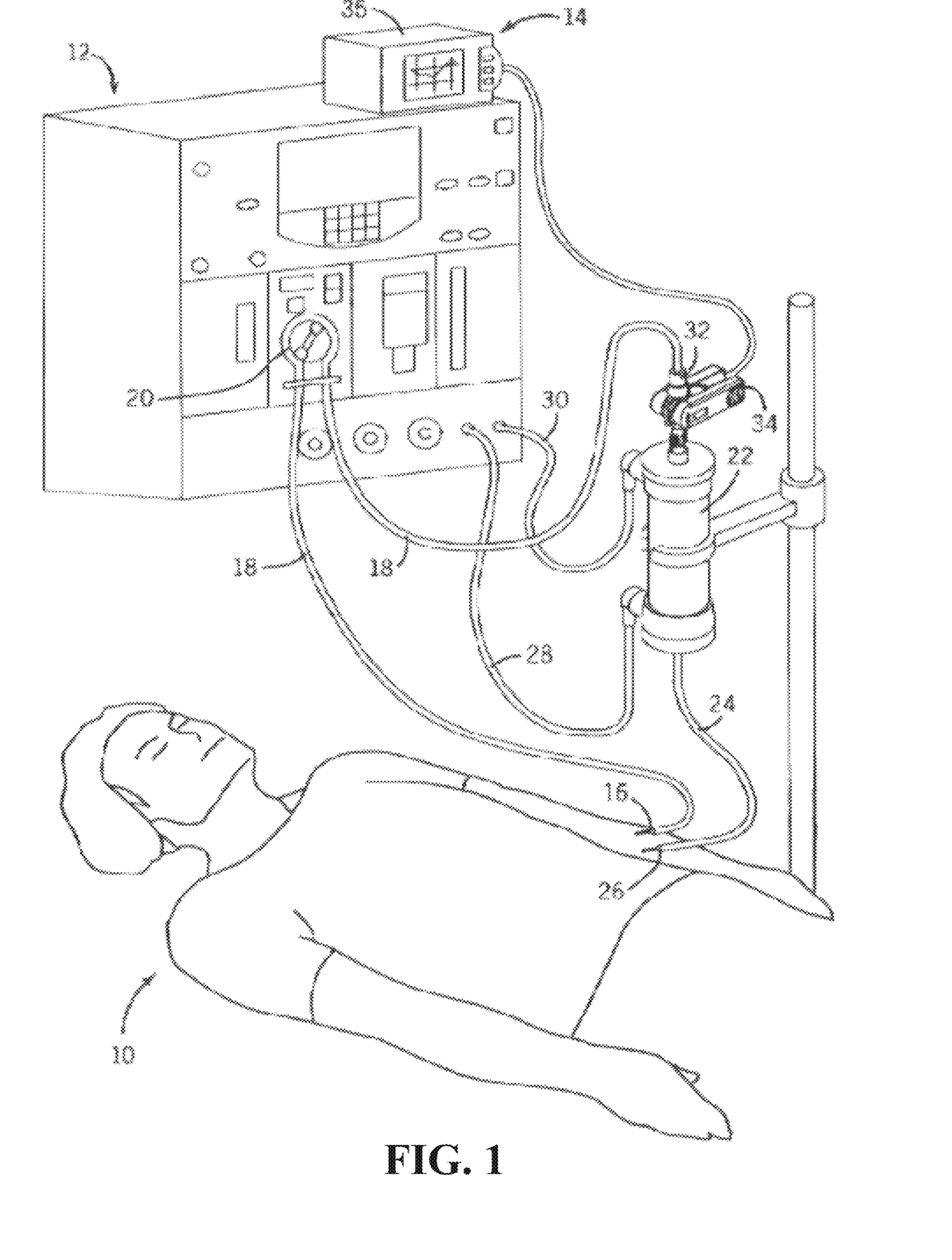
FIG. 1 is a perspective view of a typical patient undergoing hemodialysis treatment with a non-invasive, optical blood monitor monitoring the patient's blood in real-time as it passes through extracorporeal tubing in the hemodialysis system.

FIG. 1 is a perspective view of an exemplary patient undergoing hemodialysis treatment with a non-invasive, optical blood monitor monitoring the patient's blood in real-time as it passes through extracorporeal tubing in the hemodialysis system. The environment illustrated in FIG. 1 is usable with exemplary embodiments of the present disclosure. Further, it will be appreciated that the environment shown in FIG. 1 is merely exemplary, and that the principles discussed herein with respect to exemplary embodiments of the present disclosure may be implemented in other environments as well.

FIG. 1 illustrates a patient 10 undergoing hemodialysis treatment using a hemodialysis system 12, as well as a non-invasive, optical blood monitor 14. A typical hemodialysis clinic will have several hemodialysis systems 12 for treating patients on a Monday-Wednesday-Friday schedule or a Tuesday-Thursday-Saturday schedule. While the invention is not limited to the number of hemodialysis systems located at a clinic, or the specific type of hemodialysis system, the general operation of the hemodialysis system 12 is helpful for understanding the environment in which the invention is intended to operate.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed red cell blood volume is returned from the dialyzer 22 through extracorporeal tubing 24 and return needle or catheter 26. In some parts of the world (primarily the United States), the extracorporeal blood flow may additionally receive a heparin drip to prevent clotting. The excess fluids and toxins are removed by clean dialysate liquid, which is supplied to the dialyzer 22 via tube 28 and removed for disposal via tube 30. A typical hemodialysis treatment session takes about 3 to 5 hours in the United States.

In the exemplary environment depicted in FIG. 1, the optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light optical wavelengths to measure oxyhemoglobin ($HbO_2$), hemoglobin (Hb), and $H_2O$. For example, an LED, at substantially 810 nm, is isobestic for red blood cell hemoglobin. The blood chamber 32 includes lenses so that the emitters and detectors of the sensor assembly 34 can view the blood flowing through the blood chamber 32, and determine the patient's real-time hematocrit value using ratiometric techniques generally known in the prior art.

Figure 2:
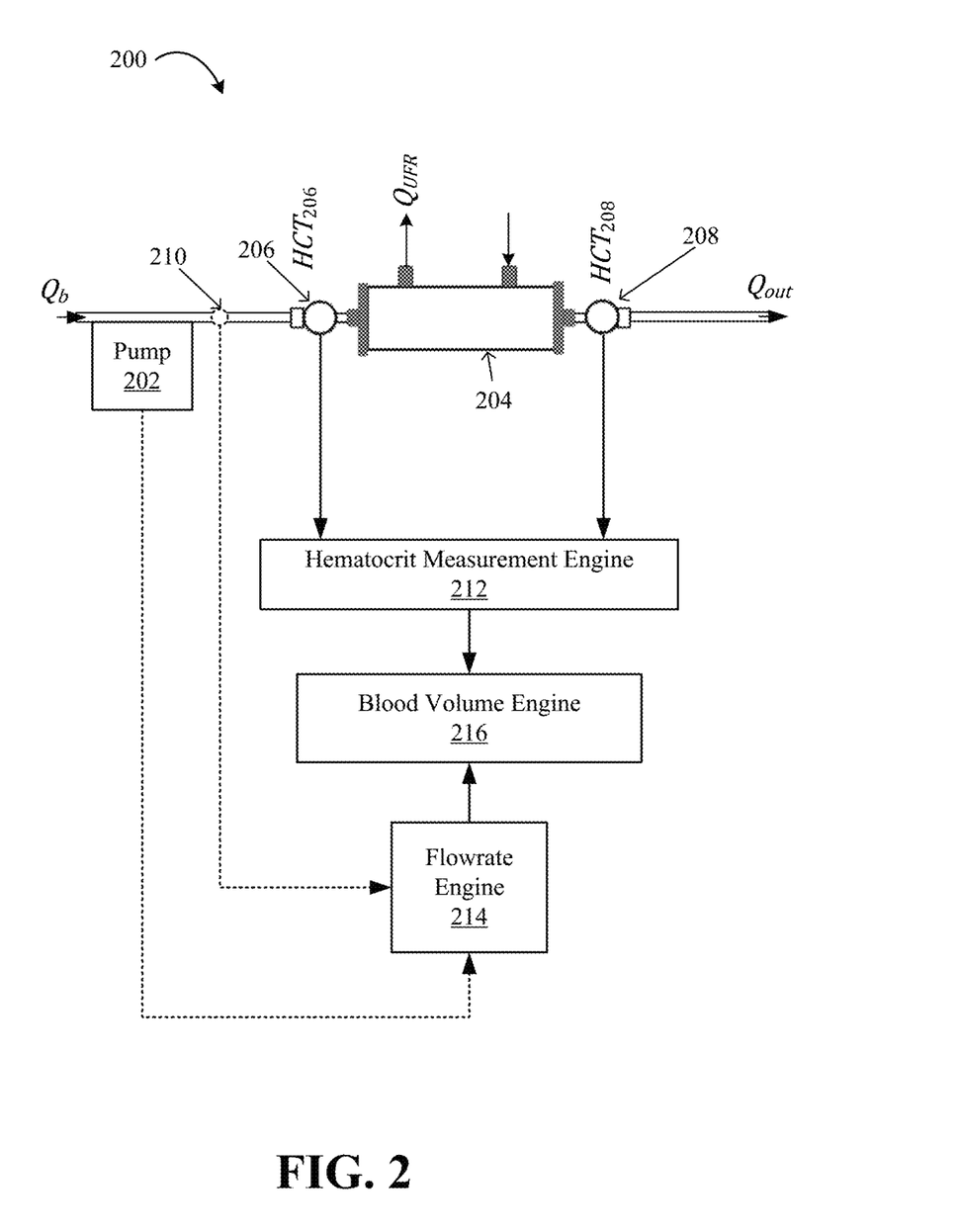
FIG. 2 illustrates an exemplary system for determining patient blood volume according to some embodiments of the disclosure.

FIG. 2 illustrates an exemplary system 200 for determining patient beginning blood volume at start of a dialysis treatment, according to some embodiments of the disclosure. The system 200 includes a hematocrit measurement engine 212, a flowrate measurement engine 214, and a blood volume engine 216.

Figure 3:
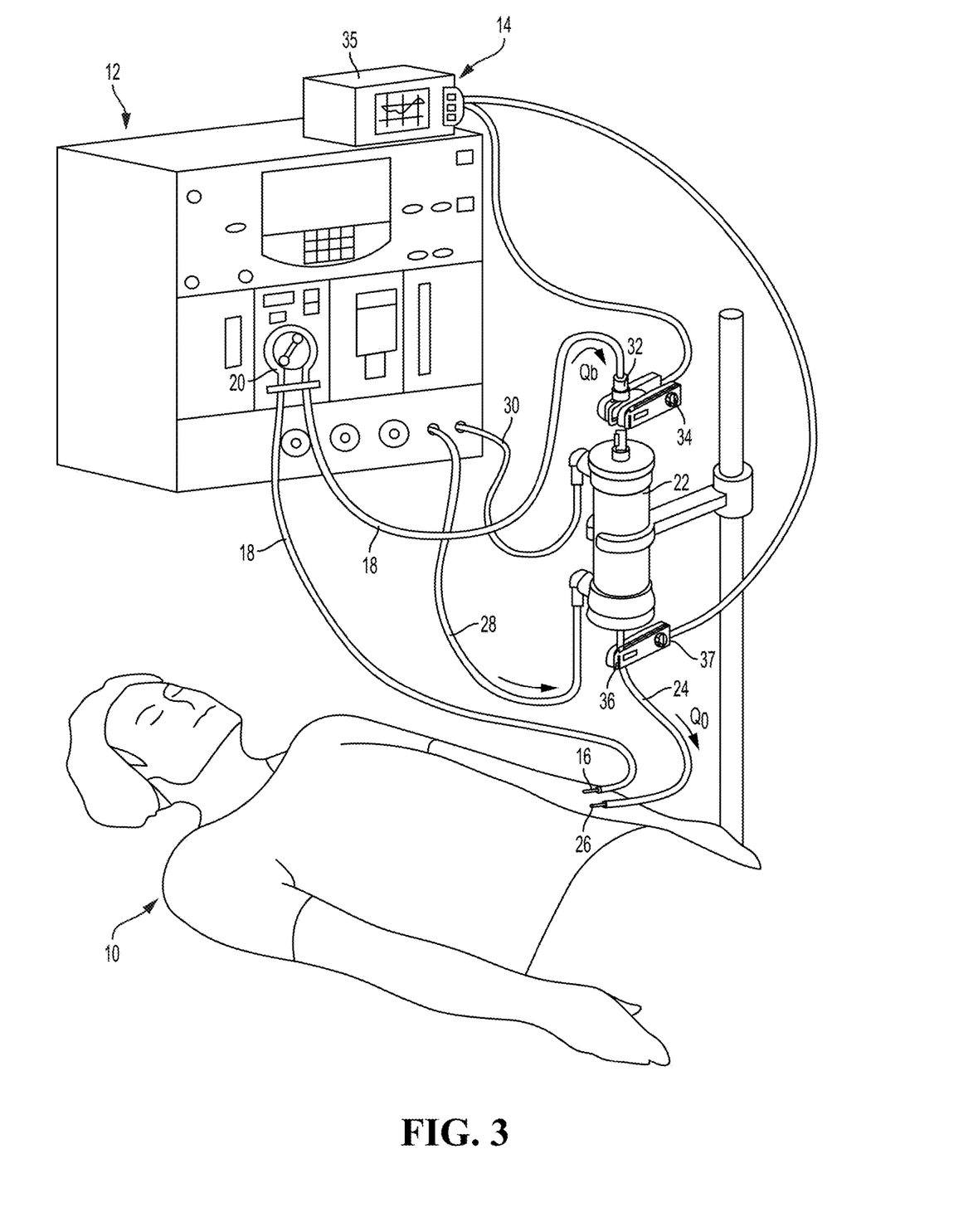
FIG. 3 illustrates a view of a patient undergoing hemodialysis treatment with a system configuration that may be used to determine patient blood volume according to some embodiments of the disclosure.

The exemplary system 200 shows a generalized embodiment which may be incorporated in the hemodialysis system 12 provided, as outlined in FIGS. 1 and 3. The hematocrit measurement engine 212, the flowrate measurement engine 214, and the blood volume engine 216 may be implemented in the hemodialysis system 12 and the non-invasive, optical blood monitor 14. In this example configuration, the flowrate measurement engine 214 may be included in the hemodialysis system 12, the hematocrit measurement engine 212 included in the optical blood monitor 14, and the blood volume engine 216 included in the optical blood monitor 14 and/or in the hemodialysis system 12. The hemodialysis system 12 and the optical blood monitor 14 can be communicably coupled to each other to realize the relationships provided in FIG. 2 for system 200, or the desired parameters can be measured independently with discrete calculations.

For an integrated embodiment, the hematocrit measurement engine 212, the flowrate measurement engine 214, and the blood volume engine 216 correspond to hardware that includes one or more processors, for example, microprocessors or microcontrollers. The hardware can also include a non-transitory computer-readable medium for temporary and/or permanent storage, for example, a read-only memory (ROM), a random access memory (RAM), a flash memory, and other computer memories and storage. Additionally, the hematocrit measurement engine 212 may utilize one or more optical blood sensor assemblies, for example, optical blood sensor assembly 34, to measure hematocrit values at both main blood flow ports of the dialyzer 204. The blood volume engine 216 may be a computing device, for example, the controller 35, that utilizes a processor and storage to determine the hematocrit values of the dialyzer 204, read the blood flowrate entering the dialyzer 204 from the processor in the dialysis machine 12, read the ultra-filtration pump rate of the dialysis machine 12 and then calculate beginning blood volume of the patient at the start of dialysis.

In the system 200 of FIG. 2, as applied to FIG. 3, blood flows into an input port of the dialyzer 204 at a blood flowrate $Q_b$. The blood flowrate is determined by the pump 202, which may be peristaltic pump 20, which is part of the dialysis machine 12 of FIG. 3. In the treatment setting of FIG. 3, blood enters the dialyzer 204, undergoes a filtration process, and filtered blood flows out of an output port of the dialyzer 204 at a blood flowrate $Q_{out}$. The difference between the blood flowrate at the input port of the dialyzer 204 and the blood flowrate at the output port of the dialyzer 204 is denoted in FIG. 2 as $Q_{UFR}$. In the treatment setting of FIG. 3, the $Q_{out}$ rate is the difference determined by the $Q_b$ rate minus the $Q_{UFR}$. The pumps on the dialysis machine 12 are calibrated, and these calibrated values are readily available during measurements. These rates can be arbitrary, but should remain the same throughout the measurements.

Multiple methods may be used to determine the flowrate $Q_b$. As shown in FIG. 2, in one embodiment, a flowmeter 210 is provisioned in the extracorporeal tubing to measure $Q_b$. The measurements from the flowmeter 210 may be provided to the flowrate engine 214.

In another exemplary embodiment, the flowmeter 210 may or may not be provided, and $Q_b$ is determined from a calibrated pumping rate of the pump 202. The pump 202 may operate at a specific number of rotations per minute, which may be matched to a commanded flowrate of blood entering the dialyzer 204. The pump 202 may provide the number of rotations per minute to the flowrate engine 214, which then determines $Q_b$ from the number of rotations per minute.

In addition to determining flowrates, the system 200 also determines hematocrit at the input port of the dialyzer 204 ($HCT_{206}$) and the output port of the dialyzer 204 ($HCT_{208}$). In one embodiment, a ratiometric technique, as disclosed in U.S. Pat. No. 5,372,136 entitled, "System and Method for Non-Invasive Hematocrit Monitoring," which is incorporated by reference in its entirety, can be used to determine hematocrit values at locations 206 and 208 in FIG. 2. If one optical blood sensor assembly 34 is used, then after measuring hematocrit at the input port of the dialyzer 204 ($HCT_{206}$), the optical blood assembly 34 is moved to measure hematocrit at the output port of the dialyzer 204 ($HCT_{208}$). If two optical blood sensor assemblies are used, then one can measure $HCT_{206}$ while the other measures $HCT_{208}$. In some embodiments, non-invasive (not requiring the pulling of samples) hematocrit measurements, for example, measurements made with the Crit-Line® system, may be used to obtain hematocrit values.

The blood volume engine 216 receives hematocrit measurements from the hematocrit measurement engine 212 and receives flowrate measurements from the flowrate engine 214. Using the hematocrit and the flowrate measurements, the blood volume engine 216 determines the total blood volume of the patient at the start of the dialysis treatment. The total blood volume of the patient at the start of dialysis treatment is determined by dividing the total blood volume of the patient removed during a treatment time by a fractional blood volume change during the same treatment time. The total blood volume removed and the fractional blood volume change are determined using the measured hematocrit values $HCT_{206}$ and $HCT_{208}$ and the blood flow rate $Q_b$.

Determination of a patient's total blood volume at time zero ($TBV_0$), at the commencement of a dialysis treatment, involves two sets of measurements since there are two unknowns, i.e., $TBV_0$ and instantaneous total blood volume at time T into the treatment, TBV(T). For performing these measurements, it is assumed that the dialysis access is viable and there is no recirculation from the venous to the arterial needles due to stenosis in or after the access.

For the first set of measurements, the fractional change in blood volume ($\Delta BV$) measured by a device such as the Crit-Line® or the Crit-Line® clip monitor (CLiC™) device must be based on calibrated blood parameters. For example, the $\Delta BV$ must be based on calibrated hematocrit values being accurate or traceable to any standard calibrated measurement of the hematocrit blood parameter.

In an embodiment, the measurement of $\Delta BV$ can be made using the CLiC™ device at location 206. A blood chamber can be placed at 206 to facilitate the measurement with the CLiC™ device. When the CLiC™ device is manufactured, each is measured on a matching blood chamber to verify accuracy of hematocrit measurements made by the device through use of human blood in the production facility's blood lab. The CLiC™ device is used here as an example of the hematocrit measurement engine 212. Since the hematocrit values measured are equivalent to laboratory hematocrit accuracy, the calibrated state of the device can be used to make a viable measurement of $\Delta BV$ at any point in time during a dialysis treatment. Hematocrit (HCT) can be defined as Eq. 1.

$$HCT = \frac{RBV}{TBV} \qquad \text{Eq. 1}$$

Where HCT is hematocrit, RBV is red blood cell volume, and TBV is total blood volume. Based on the mass balance condition where no red blood cell volume is lost in the dialyzer (only fluid is removed from the blood), calculations can be performed based on $HCT_{206}$ measured at location 206.

An initial $HCT_{206}$ can be measured at the beginning of treatment (at time T=0) before being influenced by fluid removal. The initial $HCT_{206}$ is referred to as $HCT_0$ from here on to distinguish from subsequent $HCT_{206}$ measurements. From Eq. 1, $HCT_0$ can be written as Eq. 2.

$$HCT_0 = \frac{RBV}{TBV_0} \qquad \text{Eq. 2}$$

Where $HCT_0$ is the initial hematocrit $HCT_{206}$ measured at the beginning of treatment, RBV is red blood cell volume, and $TBV_0$ is the initial total blood volume at the beginning of treatment (at time T=0).

At time duration T, a subsequent hematocrit can be measured. Hematocrit $HCT_{206}$ measured at time duration T can be defined as Eq. 3.

$$HCT(T) = \frac{RBV}{TBV(T)} \qquad \text{Eq. 3}$$

Where HCT(T) is the hematocrit $HCT_{206}$ measured at time T into the treatment, RBV is red blood cell volume, and TBV(T) is total blood volume at time T into the treatment.

Eq. 2 and Eq. 3 can be rearranged to produce Eq. 4 and Eq. 5, respectively.

$$TBV_0 = \frac{RBV}{HCT_0} \qquad \text{Eq. 4}$$

$$TBV(T) = \frac{RBV}{HCT(T)} \qquad \text{Eq. 5}$$

Since RBV is constant, Eq. 4 and Eq. 5 can be combined to calculate fractional change in blood volume $\Delta BV$ as indicated in Eq. 6.

$$\Delta BV = \frac{TBV(T) - TBV_0}{TBV_0} = \left[\frac{HCT_0}{HCT(T)} - 1\right] \qquad \text{Eq. 6}$$

The $\Delta BV$ is based on calibrated hematocrit values and is bounded by the accuracy of the hematocrit measurements. Rearranging Eq. 6 provides Eq. 7.

$$\Delta BV \times TBV_0 = TBV(T) - TBV_0$$

$$TBV(T) = TBV_0 \times (\Delta BV + 1) \qquad \text{Eq. 7}$$

Eq. 7 provides a relationship for the first set of measurements and provides a first equation involving two unknowns, both the original patient blood volume $TBV_0$ at the beginning of treatment and the patient blood volume TBV(T) at some time T into the treatment. To solve Eq. 7, a second set of measurements is determined.

The second relationship between $TBV_0$ and TBV(T) involves an approximate integration of the blood volume fluid amount removed from time zero (i.e., from time T=0). That is, the total blood removed through ultrafiltration from time zero (e.g., the start of treatment) until time T can be written as Eq. 8. Eq. 8 presents fluid removal volume based on a sampled integration technique based on timed samples.

$$TBV(T) - TBV_0 = \sum_{n=1 \, (Step \, \Delta t)}^{T/\Delta t} \left(\frac{Q_{UFR}(n) + Q_{UFR}(n-1)}{2}\right) \times \Delta t \qquad \text{Eq. 8}$$

In Eq. 8, $Q_{UFR}$ is actual fluid removal rate in the dialysis circuit based on ultrafiltration mechanisms. $Q_{UFR}$ is not the ultrafiltration rate of an ultrafiltration pump. $\Delta t$ is time between measurements of $Q_{UFR}$ along the TBV(T) history curve. The smaller $\Delta t$ becomes, the more data is processed by the blood volume engine 216 and the more accurate the integration estimation of Eq. 8 becomes. Time T is total time into the treatment in which $Q_{UFR}$ has been active. For use of Eq. 8, ultrafiltration pump rate and blood pump rate should remain at steady-state from an initial time T=0 until time T. To enhance readability, the initial time T=0 will be referred to as initial time $t_0$. In an embodiment, the floor of $T/\Delta t$ can be seen as number of measurement periods from the initial time $t_0$.

The $Q_{UFR}$ volume change is the rate of removing fluid from the blood (in the dialyzer 204) into the dialysate. This should not be confused with pump ultrafiltration rate value set for an ultrafiltration pump for circulating dialysate through the dialyzer 204. Because the fluid removal from the patient's blood is accomplished by osmosis using the dialysate liquid passing through the dialyzer 204, external to the dialyzer fibers, while blood flow is confined within the dialyzer fibers, the actual fluid volume transfer $Q_{UFR}$ is not equal to the flowrate of dialysate (ultrafiltration pump rate) passing outside the dialyzer fibers. The fluid volume transfer is dependent not only on the ultrafiltration pump rate but also on factors such as, efficiency of the dialyzer construction, chemistry makeup of the dialysate, and so on. The fluid volume rate removed from the blood $Q_{UFR}$ is an additive component to the spent dialysate volume as it passes out of the dialyzer.

Solving Eq. 8 for TBV(T) provides Eq. 9, and setting Eq. 7 equal to Eq. 9 provides Eq. 10.

$$TBV(T) = \left[\sum_{n=1 \, (Step \, \Delta t)}^{T/\Delta t} \left(\frac{Q_{UFR}(n) + Q_{UFR}(n-1)}{2}\right) \times \Delta t\right] + TBV_0 \qquad \text{Eq. 9}$$

$$TBV_0 = \frac{\left[\sum_{\substack{n=1 \\ (Step\ \Delta t)}}^{T/\Delta t} \left(\frac{Q_{UFR}(n) + Q_{UFR}(n-1)}{2}\right) \times \Delta t\right]}{\Delta BV} \quad \text{Eq. 10}$$

Thus, to determine an accurate $TBV_0$ by solving Eq. 10, actual $Q_{UFR}$ must be determined. $Q_{UFR}$ can be measured from the following outlined process:

Dialysis blood pump is calibrated and accurate in its settings for moving blood through the dialyzer blood circuit. That is, pump 202 should provide a calibrated pump volume flow $Q_b$. Commonly, pumps used in dialysis are calibrated at their factories.

During the measurement period, pump volume flow $Q_b$ should remain constant from time $t_0$ to time T.

Calibrated hematocrit sensors, e.g., Crit-Line® or CLiC™ devices, are used to measure $HCT_{206}$ and $HCT_{208}$. As previously discussed, one sensor can be used measure $HCT_{206}$ and afterwards used to measure $HCT_{208}$ for a setup in FIG. 1, or two sensors can be used to simultaneously measure both $HCT_{206}$ and $HCT_{208}$ for a setup in FIG. 3. $\Delta t$ can be used to gauge whether one sensor or two sensors will suffice. If $\Delta t$ is reasonably large, e.g., 1 sample per minute or more, a single sensor can be used to measure hematocrit at both points because dialysis parameters do not change quickly.

At a periodic time interval $\Delta t$, with the dialysis pump set to a constant and known $Q_b$, $HCT_{206}$ and $HCT_{208}$ are measured simultaneously (or near simultaneously if the hematocrit values are not changing rapidly). At the same time hematocrit measurements are made, fractional change in blood volume $\Delta BV$ is calculated using Eq. 6 and $HCT_{206}$.

Using mass balance of the red blood cell volume flowing through the dialyzer (assuming no loss of red blood cell volume during time T), the following relationships can be derived to solve for $Q_{UFR}$. Beginning at location 206:

$$HCT_{206} = \frac{RBVR}{Q_b} \quad \text{Eq. 11}$$

Where $HCT_{206}$ is calibrated measured hematocrit at location 206, RBVR is red blood cell volume rate flowing through the dialyzer, and $Q_b$ is blood flow rate dictated by a calibrated blood pump. A similar relationship can be written at location 208 as:

$$HCT_{208} = \frac{RBVR}{Q_b - Q_{UFR}} \quad \text{Eq. 12}$$

Where $HCT_{208}$ is calibrated measured hematocrit at location 208, RBVR is red blood cell volume rate flowing through the dialyzer, $Q_b$ is calibrated blood flowrate, and $Q_{UFR}$ is true fluid removal volume rate.

Embodiments of the disclosure use the hematocrit monitoring engine 212 to measure the hematocrit of the blood entering the dialyzer 204 and then the HCT blood exiting the dialyzer 204. Due to the nature of the dialyzer 204, no red blood cells are lost across dialyzer membranes within the dialyzer 204—only fluid, for example, urea, passes through into the waste collecting dialysate. Since red blood cells do not cross the dialyzer membranes into the waste, mass balance analysis of the red blood cell volume is applicable.

Assuming red blood cell volume is constant (i.e., no red blood cell volume is lost during time T), then Eqs. 11 and 12 can be combined to provide Eq. 13:

$$HCT_{206} \times Q_b = HCT_{208} \times (Q_b - Q_{UFR}) \quad \text{Eq. 13}$$

Eq. 13 can be rearranged as Eq. 14.

$$Q_{UFR} = \left(\frac{HCT_{208} - HCT_{206}}{HCT_{208}}\right) \times Q_b \quad \text{Eq. 14}$$

Since $HCT_{208}$ and $HCT_{206}$ are calibrated hematocrit values and $Q_b$ is a calibrated flow rate of the blood pump 202, $Q_{UFR}$, which is derived from the calibrated values of $HCT_{208}$, $HCT_{206}$, and $Q_b$, is also a calibrated value. Values of $Q_{UFR}$ obtained and used at samples $n=0$ through $n=\lfloor T/\Delta t \rfloor$ with sampling rate of $\Delta t$, can be used in Eq. 10 to calculate a number of solutions for $TBV_0$. Successive values of calculated $TBV_0$ at each measurement time $n\Delta t$ can be averaged to improve accuracy of $TBV_0$ obtained.

The blood volume engine 216 determines $TBV_0$ using relationships shown in Eq. 10 and Eq. 14, depending on information received from the hematocrit measurement engine 212 and the flowrate engine 214. Note that in FIG. 2, dotted lines represent potential alternative inputs for determining flowrate, some or all of which may be used in different exemplary embodiments. For example, the blood flowrate at the input of the dialyzer 204 is desired, but this flowrate can be determined from either the calibrated pump 202 or the flowmeter 210, thus one of these measurement paths may be active and the other inactive.

Figure 4:
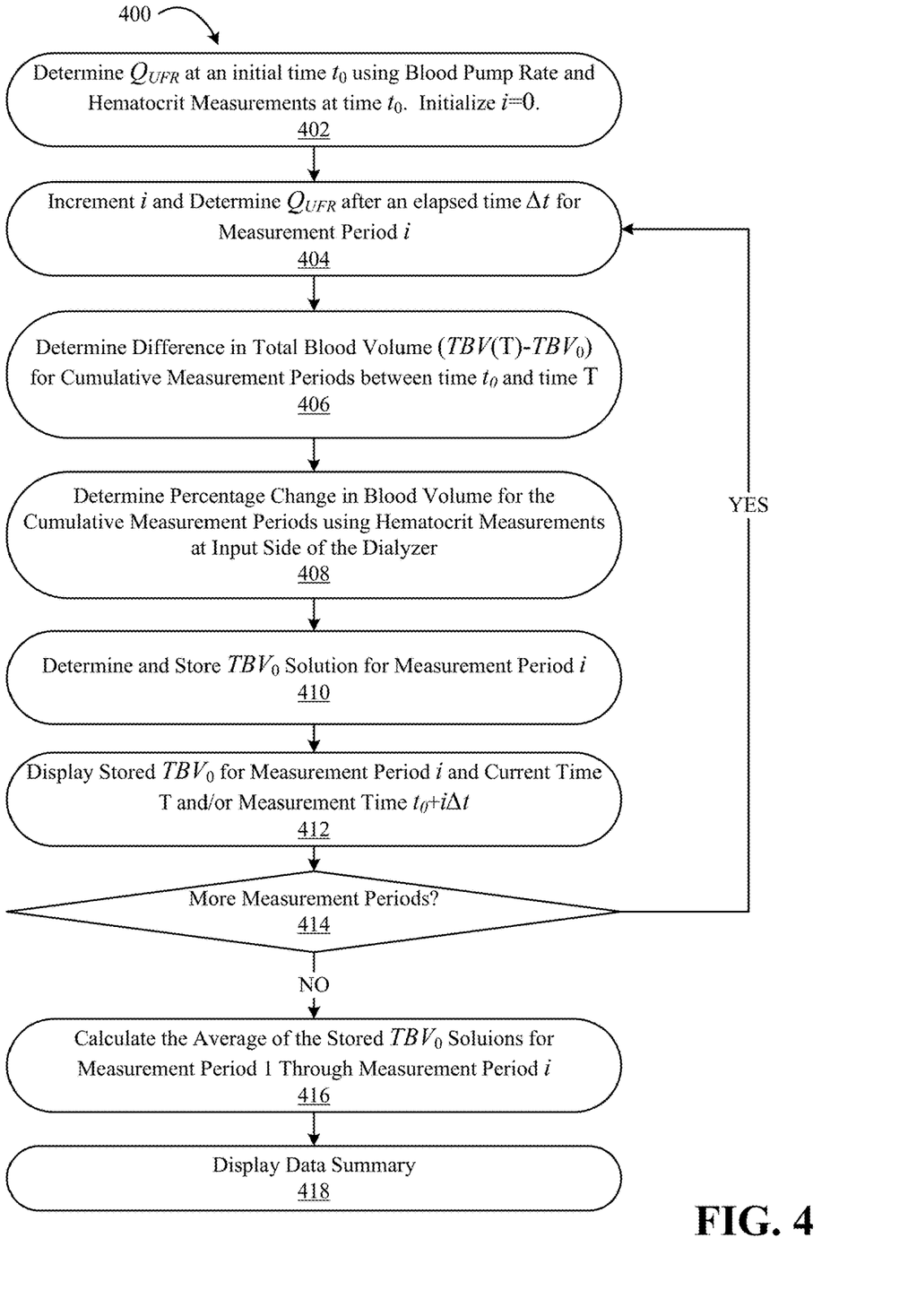
FIG. 4 illustrates a process for determining patient blood volume according to some embodiments of the disclosure.

FIG. 4 illustrates a process 400 for determining patient blood volume, according to some embodiments of the disclosure. At step 402, the system 200 determines $Q_{UFR}$ (actual fluid removal rate) at an initial time $t_0$ using $Q_b$ (calibrated blood flowrate) and hematocrit measurements $HCT_{206}$ and $HCT_{208}$ at the time $t_0$. The blood volume engine 216 determines $Q_{UFR}$ at time $t_0$ according to Eq. 14 using $HCT_{206}$ and $HCT_{208}$ at the time $t_0$ from the hematocrit measurement engine 212 and $Q_b$ from the flowrate engine 214. The $Q_{UFR}$ measured is associated with time $t_0$, and a temporary variable $i=\lfloor T/\Delta t \rfloor$ is used to keep track of total number of measurement periods, a current or most recent measurement period, or a total number of $TBV_0$ measurements taken. Initially, at time $T=0$, i is 0, and i only becomes 1 after a time period $\Delta t$ has passed. That is, once T reaches $\Delta t$.

At step 404, after an elapsed time $\Delta t$, the blood volume engine 216 automatically increments i, based on the mathematical relationship above, and determines $Q_{UFR}$ in a similar manner as already discussed with respect to step 402. The $Q_{UFR}$ determined at 404 is $Q_{UFR}$ for the measurement period i.

At step 406, the blood volume engine 216 determines difference in total blood volume for cumulative measurement periods between time $t_0$ (T=0) and time T. That is, the blood volume engine 216 determines fluid removed during a total number of elapsed measurement periods in the time T. Referring to Eq. 8, volume removed during a single measurement period involves adding a previous $Q_{UFR}$ and a current $Q_{UFR}$, dividing the result of the addition by 2, and then multiplying the result by the duration $\Delta t$ between the $Q_{UFR}$ measurements. That is, volume removed in measurement period i is determined using $Q_{UFR}$ for measurement period i-1. $Q_{UFR}$ for measurement period i, and $\Delta t$, time duration between $Q_{UFR}$ measurements for periods i-1 and i.

The volume removed in measurement period i is then added to total volume removed from time $t_0$ until measurement period i−1 to obtain total blood volume removed for cumulative measurement periods between time $t_0$ and T.

For illustrative purposes, an example is provided. At time $t_0$, total volume removed is 0. At measurement period 1, volume removed is calculated to be $TBV(1\Delta t)-TBV_0$. This value, $TBV(1\Delta t)-TBV_0$, is added to the previous total volume removed, 0, to obtain current total volume removed, $TBV(1\Delta t)-TBV_0$. At measurement period 2, volume removed is calculated to be $TBV(2\Delta t)-TBV(1\Delta t)$. This value, $TBV(2\Delta t)-TBV(1\Delta t)$, is added to the previous total volume removed, $TBV(1\Delta t)-TBV_0$, to obtain the current total volume removed $TBV(2\Delta t)-TBV_0$. In this manner, through every successive measurement period, a difference of volume removed for a most recent measurement period is continually calculated and added to a running total of blood volume removed. At 406, the blood volume engine 216 thus determines fluid removed for cumulative measurement periods from initial time $t_0$ until a most recent time T.

At step 408, the blood volume engine 216 determines percentage change in blood volume or fractional change in blood volume $\Delta BV$ for the cumulative measurement periods. The $\Delta BV$ is determined according to Eq. 6, with $HCT_0$ being $HCT_{206}$ at initial time $t_0$ and HCT(T) being $HCT_{206}$ for the most recent measurement period i. Since measurements are made at sample intervals $\Delta t$, note that HCT(T) for the most recent measurement period i corresponds to HCT($\Delta t$).

At step 410, the blood volume engine 216 determines and stores $TBV_0$ solution for the current measurement period i. The blood volume engine 216 determines the beginning blood volume of the patient $TBV_0$, as defined in Eq. 10, using the $\Delta BV$ from step 408 and the difference in total blood volume from step 406.

At step 412, the blood volume engine 216 displays stored $TBV_0$ for measurement period i and current time T and/or time when the measurement was taken i$\Delta t$.

At step 414, the blood volume engine 216 determines whether there are more measurement periods. If there are more measurements to be made, then a new $Q_{UFR}$ measurement is made at step 404 and i is incremented, otherwise the blood volume engine 216 determines, at step 416, an average of the stored $TBV_0$ solutions for measurement period 1 through measurement period i.

At step 418, the blood volume engine 216 displays data summary of all measurements made during the process 400.

Based on the value that a user obtains from the output of the hemodialysis system 12, the user may determine a treatment plan for the patient or know how aggressive the dialysis treatment should be. If the patient's beginning blood volume differs significantly from previous visits, the user (physician) can further provide additional tips to the patient on managing the total blood volume.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system for determining beginning blood volume of a patient undergoing dialysis treatment, the system comprising:
    a first portion of tubing, configured to connect a patient to an input port of a dialyzer;
    a second portion of tubing, configured to connect the patient to an output port of the dialyzer;
    a pump, configured to pump blood from the patient through the first portion of tubing into the dialyzer, and out of the dialyzer into the second portion of tubing;
    a first blood chamber, disposed along the first portion of tubing, and a second blood chamber, disposed along the second portion of tubing;
    a sensor assembly configured to obtain sensor measurements;
    a controller; and
    a non-transitory computer-readable medium having processor-executable instructions stored thereon, wherein the processor-executable instructions, when executed by the controller, facilitate:
        determining the beginning blood volume using hematocrit values associated with the input port of the dialyzer, hematocrit values associated with the output port of the dialyzer, and a flowrate of blood through the first portion of tubing, wherein the beginning blood volume is a blood volume of the patient at the start of the dialysis treatment.

2. The system according to claim 1, wherein the processor-executable instructions, when executed by the controller, further facilitate:

determining the flowrate of blood through the first portion of tubing through a calibrated pumping rate of the pump.

3. The system according to claim 1, further comprising:
at least one flowmeter coupled to the first portion of tubing, the at least one flowmeter configured to determine the flowrate of blood through the first portion of tubing.

4. The system according to claim 1, wherein the sensor assembly comprises:
a first sensor assembly coupled to the first blood chamber, the first sensor assembly configured to measure hematocrit values associated with the input port of the dialyzer; and
a second sensor assembly coupled to the second blood chamber, the second sensor assembly configured to measure hematocrit values associated with the output port of the dialyzer.

5. The system according to claim 1, wherein the processor-executable instructions, when executed by the controller, further facilitate:
determining a fractional change in patient blood volume using a hematocrit value associated with the input port of the dialyzer at the beginning of the dialysis treatment and a hematocrit value associated with the input port of the dialyzer at an end of a measurement session;
determining a plurality of fluid removal volume rates during the measurement session using the hematocrit values associated with the input port of the dialyzer, the hematocrit values associated with the output port of the dialyzer, and the flowrate of blood through the first portion of tubing; and
determining the beginning blood volume based on the fractional change in patient blood volume and the plurality of fluid removal volume rates.

6. The system according to claim 5, wherein the processor-executable instructions, when executed by the controller, further facilitate:
determining an initial fluid removal volume rate in the plurality of fluid removal volume rates; and
determining each successive fluid removal volume rates in the plurality of fluid removal volume rates at a sample interval.

7. The system according to claim 6, wherein the sample interval is 1 minute or longer.

8. The system according to claim 5, wherein the processor-executable instructions, when executed by the controller, further facilitate:
determining that the beginning blood volume is an average of a plurality of beginning blood volumes corresponding to the plurality of fluid removal volume rates;
wherein a number of the plurality of beginning blood volumes is at least 2 and a number of the plurality of fluid removal volume rates is at least 3.

\* \* \* \* \*